United States Patent
Annegarn et al.

(10) Patent No.: US 10,335,059 B2
(45) Date of Patent: Jul. 2, 2019

(54) FALL DETECTION SYSTEM AND METHOD

(71) Applicant: KONINKLIJKE PHILIPS N.V., Eindhoven (NL)

(72) Inventors: Janneke Annegarn, Eindhoven (NL); Warner Rudoph Theophile Ten Kate, Waalre (NL); Heribert Baldus, Aachen (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 79 days.

(21) Appl. No.: 14/917,603

(22) PCT Filed: Aug. 28, 2014

(86) PCT No.: PCT/EP2014/068209
§ 371 (c)(1),
(2) Date: Mar. 9, 2016

(87) PCT Pub. No.: WO2015/036245
PCT Pub. Date: Mar. 19, 2015

(65) Prior Publication Data
US 2016/0220153 A1    Aug. 4, 2016

(30) Foreign Application Priority Data
Sep. 11, 2013  (EP) ..................................... 13183914

(51) Int. Cl.
*A61B 5/11* (2006.01)
*G08B 21/04* (2006.01)
(Continued)

(52) U.S. Cl.
CPC ........... *A61B 5/1117* (2013.01); *A61B 5/1118* (2013.01); *A61B 5/7275* (2013.01);
(Continued)

(58) Field of Classification Search
CPC .............. A61B 5/02438; A61B 5/1117; A61B 5/1118; A61B 5/112; A61B 5/1123
(Continued)

(56) References Cited

U.S. PATENT DOCUMENTS 6,864,796 B2 *  3/2005  Lehrman .............. A61B 5/0205
                                                    340/426.15
7,145,461 B2 * 12/2006  Lehrman .............. A61B 5/0205
                                                    340/426.1
(Continued)

FOREIGN PATENT DOCUMENTS

EP        2264988 A1    12/2010
JP     2006228024 A      8/2006
(Continued)

OTHER PUBLICATIONS

Helbostad et al: "Physical Fatigue Affects Gait Characteristics in Older Persons"; Journal of Gerontology:Medical Sciences, 2007, vol. 62A, No. 9, pp. 1010-1015.
(Continued)

*Primary Examiner* — May A Abouelela

(57) ABSTRACT

There is provided a fall detection system for use in detecting falls by a user, the fall detection system comprising a processing unit configured to determine context information about the user and/or the environment in which the user is located, and to increase the sensitivity of a fall detection algorithm used to detect falls by a user in the event that the determined context information indicates that the user is or may be at an increased risk of falling, the increase in sensitivity occurring while the increased risk of falling is indicated by the determined context information.

21 Claims, 9 Drawing Sheets

(51) Int. Cl.
*G08B 29/18* (2006.01)
*A61B 5/00* (2006.01)
*G01P 13/00* (2006.01)
*G08B 29/20* (2006.01)

(52) U.S. Cl.
CPC ............ *G01P 13/00* (2013.01); *G08B 21/043* (2013.01); *G08B 21/0446* (2013.01); *G08B 29/185* (2013.01); *A61B 2560/0223* (2013.01); *A61B 2560/0242* (2013.01); *A61B 2562/0219* (2013.01); *G08B 29/20* (2013.01)

(58) Field of Classification Search
USPC ................... 600/300, 587, 595; 340/539.12
See application file for complete search history.

(56) References Cited

U.S. PATENT DOCUMENTS

| | | | |
|---|---|---|---|
| 7,282,031 B2 | 10/2007 | Hendrich | |
| 7,857,771 B2* | 12/2010 | Alwan | A61B 5/1038 340/573.1 |
| 7,988,647 B2* | 8/2011 | Bunn | A61B 5/1038 600/587 |
| 8,206,325 B1* | 6/2012 | Najafi | A61B 5/1117 600/587 |
| 8,381,603 B2* | 2/2013 | Peng | A61B 5/1117 600/587 |
| 8,408,041 B2* | 4/2013 | Ten Kate | A61B 5/1117 600/587 |
| 8,747,336 B2* | 6/2014 | Tran | G06F 19/3418 600/300 |
| 9,005,141 B1* | 4/2015 | Najafi | A61B 5/1117 600/587 |
| 2006/0241521 A1* | 10/2006 | Cohen | A61B 5/0002 600/595 |
| 2006/0282021 A1* | 12/2006 | DeVaul | A61B 5/0024 600/595 |
| 2007/0038155 A1* | 2/2007 | Kelly, Jr. | A61B 5/1117 600/595 |
| 2007/0118054 A1* | 5/2007 | Pinhas | A61B 5/1104 600/587 |
| 2009/0318779 A1* | 12/2009 | Tran | A61B 5/0022 600/301 |
| 2010/0049096 A1* | 2/2010 | Ten Kate | A61B 5/1117 600/595 |
| 2010/0056957 A1* | 3/2010 | Vuillerme | A61B 5/1116 600/587 |
| 2010/0286567 A1* | 11/2010 | Wolfe | A61B 5/1117 600/587 |
| 2010/0298661 A1* | 11/2010 | McCombie | G06F 19/3437 600/301 |
| 2011/0152727 A1* | 6/2011 | Ten Kate | A61B 5/1117 600/595 |
| 2011/0201972 A1* | 8/2011 | Ten Kate | G08B 21/0446 600/595 |
| 2011/0230791 A1* | 9/2011 | Ten Kate | G08B 21/0446 600/595 |
| 2012/0016270 A1* | 1/2012 | Buhler | A61B 5/1117 600/595 |
| 2012/0092169 A1 | 4/2012 | Kaiser et al. | |
| 2012/0095722 A1 | 4/2012 | Ten Kate | |
| 2012/0119904 A1 | 5/2012 | Coleman Boone et al. | |
| 2012/0123277 A1* | 5/2012 | Blaha | G06K 9/00067 600/476 |
| 2012/0190949 A1 | 7/2012 | McCombie et al. | |
| 2012/0245464 A1* | 9/2012 | Tran | A61B 5/021 600/437 |
| 2013/0023798 A1 | 1/2013 | Greene et al. | |
| 2013/0060167 A1 | 3/2013 | Dracup et al. | |
| 2013/0172691 A1* | 7/2013 | Tran | A61B 8/488 600/301 |
| 2013/0211291 A1* | 8/2013 | Tran | G06F 19/3418 600/595 |
| 2013/0274565 A1* | 10/2013 | Langer | A61N 1/3993 600/301 |
| 2014/0194702 A1* | 7/2014 | Tran | A61B 8/06 600/301 |
| 2014/0228712 A1* | 8/2014 | Elliott | A63B 71/06 600/587 |
| 2014/0303523 A1* | 10/2014 | Hong | A61B 5/4866 600/595 |
| 2014/0316305 A1* | 10/2014 | Venkatraman | A61B 5/1112 600/595 |
| 2015/0313552 A1* | 11/2015 | Zhang | A61B 5/1117 600/595 |

FOREIGN PATENT DOCUMENTS

| | | |
|---|---|---|
| JP | 2010539617 A | 12/2010 |
| JP | 2011161208 A | 8/2011 |
| JP | 2012502341 A | 1/2012 |
| JP | 2012532652 A | 12/2012 |
| WO | 2004114245 A1 | 12/2004 |
| WO | 2009037612 A2 | 3/2009 |
| WO | 2009156936 A2 | 12/2009 |
| WO | 2010023604 A1 | 3/2010 |
| WO | 2010026513 A1 | 3/2010 |
| WO | 2011004322 A1 | 1/2011 |
| WO | 2013190484 A1 | 12/2013 |

OTHER PUBLICATIONS

Srygley et al: "Self-Report of Missteps in Older Adults: A Valid Proxy of Fall Risk?"; Arch Phys Med Rehabil, vol. 90, May 2009, pp. 786-792.

Tinetti et al: "The Patient Who Falls: It's Always a Trade-Off"; JAMA, Jan. 20, 2010—vol. 303, No. 3, pp. 258-266.

Zhang et al: "Context-Aware Fall Detection Using a Bayesian Network"; Proceedings of the 5th ACM International Workshop on Context-Awareness for Self-Managing System, 2011, pp. 10-16.

* cited by examiner

FALL DETECTION SYSTEM AND METHOD

CROSS-REFERENCE TO PRIOR APPLICATIONS

This application is the U.S. National Phase application under 35 U.S.C. § 371 of International Application No. PCT/IB2014/068209, filed on Aug. 28, 2014, which claims the benefit of European Patent Application No. 13183914.4, filed on Sep. 11, 2013. These applications are hereby incorporated by reference in their entirety herein.

TECHNICAL FIELD OF THE INVENTION

The invention relates to a fall detection system that is for detecting falls by a user.

BACKGROUND TO THE INVENTION

Falls affect millions of people each year and result in significant injuries, particularly among the elderly. In fact, it has been estimated that falls are one of the top three causes of death in elderly people. A fall is defined as a sudden, uncontrolled and unintentional downward displacement of the body to the ground, followed by an impact, after which the body stays down on the ground.

A personal emergency response system (PERS) is a system in which help for a user can be assured. By means of Personal Help Buttons (PHBs) the user can push the button to summon help in an emergency. A majority of calls are because the user has fallen. Also, if the user suffers a severe fall (for example by which they get confused or even worse if they are knocked unconscious), the user might be unable to push the button, which might mean that help doesn't arrive for a significant period of time, particularly if the user lives alone. The consequences of a fall can become more severe if the user stays lying for a long time.

Fall detection systems are also available that process the output of one or more movement sensors to determine if the user has suffered a fall. Most existing body-worn fall detection systems make use of an accelerometer (usually an accelerometer that measures acceleration in three dimensions) and they are configured to infer the occurrence of a fall by processing the time series generated by the accelerometer. Some fall detection systems can also include an air pressure sensor, for example as described in WO 2004/114245, for measuring the height, height change or absolute altitude of the fall detection system. On detecting a fall, an alarm is triggered by the fall detection system.

Some fall detection systems are designed to be worn as a pendant around the neck of the user, whereas others are designed to be worn on or at the torso (e.g. waist, on a waist belt or in a pocket) or on the limbs of the user, for example at the wrist.

A lot of effort is being put into providing robust classification methods or processing algorithms for detecting falls accurately. In general, a fall detector tests on features like impact, orientation, orientation change, height change, vertical velocity, and alike. Reliable detection results when the set of computed values for these features is different for falls than for other movements that are not a fall. The algorithm can compare the detected features with predetermined threshold values and/or classification patterns to determine if a fall event has occurred.

The reliability of the classification method can be visualized by a receiver operating characteristic (ROC) curve in which the detection probability is plotted against the false alarm rate. FIG. 1 shows such ROC-curve which represents the average performance of the algorithm across many users tested over a long time period. The optimal trade-off between detected falls and false alarms (the 'operating point') depends on several factors, such as customer/user satisfaction and economic factors. A high rate of false alarms is costly for the service centre and annoying to the customer (user), whereas diminishing the amount of false alarms may lead to missed falls which can be extremely troublesome or harmful to the customer (user). It is the aim of the fall detection algorithm designer to create an algorithm with an operating point that reaches the upper-left corner of the ROC curve as closely as possible. However, the precise operating point can depend on the mentioned external conditions and preferences.

In general, people with a low fall risk are more active and may generate more movements in daily life that appear to the fall detection algorithm as falls. As a consequence, the amount of false alarms may be higher than average for this 'low fall risk' group, while the amount of actual falls is lower than average. FIGS. 2 and 3 show exemplary relationships between false alarm rate/true falls and the fall risk/activity level respectively. The curves may take other shapes. For example, the false alarm rate may have a maximum half way in both graphs.

SUMMARY OF THE INVENTION

Besides the movement behaviour in daily life, also the movement behaviour during a fall can differ between people with a low and high fall risk. The 'low fall risk' group is in general able to correct small balance disturbances during slow movements. Therefore most falls in this group happen as a consequence of fast movements and/or large balance disturbances resulting in a relatively high impact when the person contacts the ground. The 'high fall risk' group generally move more slowly and more carefully. Falls can also occur when the person is standing still and they gradually lose balance but are unable to correct for it. However, such a user may make some effort to maintain balance and grasp around for support while falling, which can lead to the user contacting the ground with a relatively low impact. For this reason different ROC-curves can be drawn for people with different levels of fall risk. Due to differences in movement behaviour, the optimal classification method, the resulting ROC-curve and/or the optimal operating point on the ROC-curve depends on the dynamic fall risk of a user. FIG. 4 shows exemplary ROC-curves for two different types of user groups (low fall risk users and high fall risk users). Different ROC-curves could also be drawn for users who wear the fall detection system below their clothing and over their clothing, for example, or for users with different characteristics, such as height, which lead to different height drops during a fall. It can be seen that the incidence of falls and false alarms as well as the detection probability change distribution, and this also changes the optimal fall detector design.

It has been found that some of the strongest risk indicators for falling include the occurrence of previous falls by the user as well as their strength, gait and balance impairments. The ROC-curve shown in FIG. 4 does not only differ between users with different physical capabilities and previous falls, but also depends on the situation (context) of the user or their environment at a certain moment. In particular, a user's fall risk changes dynamically over time, and fall risk assessment needs to be an ongoing process. A person may be in the 'low risk' category at one point of time (e.g. while sat down talking to friends) and in the 'high risk' category at another time point (e.g. after taking medication, using the bathroom, when lights are dimmed, etc.). In some cases, the user's balance ability may be deliberately challenged or tested, for example when a user is testing their balance as part of an assessment or training or exercising to improve their ability. It is also known that the majority of falls occur during walking, and so walking is an inherently 'higher risk' activity. Also, a user with a low fall risk (for example the lights are on) generates more false alarms (since they are more active when the lights are on or during day time) while less falls are missed (since users probably fall when the lights are on due to larger disturbances and therefore the impact is high enough to be detected). A person with a high fall risk (for example the lights are off) generates less false alarms (since for example the user is sleeping for most of this time) and less falls are detected (since the user may already fall due to a very small disturbance resulting in a low impact).

It will be appreciated from the above discussion that it is not possible to configure the fall detection algorithm to operate at an optimum point on the ROC curve for all users and in all situations.

Thus, the invention provides that the sensitivity of the fall detection algorithm is adapted using contextual information about the user and/or the user's environment. In particular, if the contextual information indicates that the user is at a higher risk of falling, the sensitivity of the fall detection algorithm is increased. Preferably the increase in sensitivity is temporary and only lasts while the higher risk of falling is present or detected, after which the sensitivity of the fall detection algorithm is returned to or close to the previous (e.g. default) sensitivity for the user. In preferred embodiments, the sensitivity of the fall detection algorithm is adjusted by moving the operating point on the ROC curve. Thus, when a user is in a situation that poses a higher risk of falling, the operating point is moved temporarily to raise detection probability. In these cases it is accepted that this adapted setting also increases the probability of false alarms occurring, since the aim is to ensure that no falls are missed. Since the fall detection algorithm is only configured to be more sensitive for a short time period, a relatively low false alarm rate is still obtained on average, while reducing the chance of a fall being missed when the user is at higher risk of falling.

According to a first aspect of the invention, there is provided a method of operating a fall detection system to detect falls by a user, the method comprising determining context information about the user and/or the environment in which the user is located; and, in the event that the determined context information indicates that the user is or may be at an increased risk of falling, increasing the sensitivity of a fall detection algorithm used to detect falls by a user while the increased risk of falling is indicated by the determined context information.

In some embodiments, the context information comprises an indication of whether the user is performing a fall risk assessment test or balance training; and the context information indicates that the user is or may be at an increased risk of falling if the user is performing a fall risk assessment test or balance training.

In some embodiments, the context information comprises an indication of whether the user is walking, and the context information indicates that the user is or may be at an increased risk of falling if the user is walking.

In some embodiments, the context information comprises an indication of whether an unusual movement pattern for the user has been detected, and the context information indicates that the user is or may be at an increased risk of falling if an unusual movement pattern is detected.

In some embodiments, the context information comprises an indication of the current location of the user, and the context information indicates that the user is or may be at increased risk of falling if the current location of the user is a known location where the user is at a higher risk of falling. The known locations where the user is at a higher risk of falling may include any one or more of, a bathroom, on the stairs, outdoors or a location where the user and/or other users have previously fallen.

In some embodiments, the context information about the environment in which the user is located comprises an indication of the ambient light in the user's location, an indication of how even or uneven the ground is, an indication of the current weather or temperature and/or an indication of the ambient noise level and the context information indicates that the user is or may be at increased risk of falling if the ambient light is below a threshold, if the ground is uneven, if the weather is wet or the temperature is below a threshold and/or if ambient noise level is above threshold.

In some embodiments, the context information comprises an indication of the current time, and the context information indicates that the user is or may be at increased risk of falling if the current time is within one or more specified time periods. The one or more specified time periods may include the night time and/or time periods shortly before and/or after a scheduled dose of medication.

In some embodiments, the context information comprises an indication of the current activity level of the user, and the context information indicates that the user is or may be at increased risk of falling if the current activity level is above a threshold activity level.

In some embodiments, the step of increasing the sensitivity of a fall detection algorithm comprises increasing the likelihood that a fall will be detected.

In some embodiments, the step of increasing the sensitivity of a fall detection algorithm comprises adjusting the position of an operating point for the algorithm on a receiver operating characteristic curve.

In some embodiments, the step of increasing the sensitivity of the fall detection algorithm comprises decreasing the threshold at which the likelihood for a fall has to outweigh the likelihood for a non-fall for a fall to be detected.

In other embodiments, the step of increasing the sensitivity of a fall detection algorithm comprises determining a required operating point for the algorithm on a receiver operating characteristic curve, and selecting a configuration of the fall detection algorithm having the required operating point.

In other embodiments, the fall detection algorithm comprises determining one or more feature values from measurements of the movements of the user and comparing the one or more feature values to respective thresholds to detect if a fall has occurred, and wherein the step of increasing the sensitivity of the fall detection algorithm comprises adjusting one or more of the thresholds to increase the likelihood that a fall will be detected.

In other embodiments, the fall detection algorithm comprises determining a plurality of feature values from measurements of the movements of the user; and comparing the set of feature values to a threshold to detect if a fall has occurred, and wherein the step of increasing the sensitivity of the fall detection algorithm comprises adjusting the threshold to increase the likelihood that a fall will be detected.

In other embodiments, the fall detection algorithm comprises determining one or more feature values from measurements of the movements of the user, determining a value indicating the likelihood that the set of feature values represents a fall and a value indicating the likelihood that the set of feature values does not represent a fall, determining a ratio of the likelihood values and comparing the logarithm of the ratio to a threshold to detect if a fall has occurred, and wherein the step of increasing the sensitivity of the fall detection algorithm comprises adjusting the threshold to increase the likelihood that a fall will be detected.

In some embodiments, the fall detection algorithm comprises determining one or more feature values from measurements of the movements of the user in two or more stages, with each stage only being performed if the feature value or values determined in the previous stage indicate that a fall may have occurred, and wherein the step of increasing the sensitivity of the fall detection algorithm comprises changing the feature value or values determined in one or more stages, and/or adjusting one or more threshold values to which the feature values are compared.

In some embodiments, the method further comprising the steps of determining further context information about the user and/or the environment in which the user is located; and resetting or reducing the sensitivity of the fall detection algorithm if the further context information indicates that the user is no longer at an increased risk of falling.

In some embodiments, the method further comprises the step of initially operating the fall detection system with the fall detection algorithm set to a normal sensitivity corresponding to a normal risk of falling for the user; wherein when the context information indicates that the user is or may be at an increased risk of falling relative to the normal risk of falling for the user, the sensitivity of the fall detection algorithm is increased above the normal sensitivity.

In some embodiments, in the event that the determined context information indicates that the user is or may be at a decreased risk of falling, the method comprises the step of decreasing the sensitivity of a fall detection algorithm used to detect falls by a user while the decreased risk of falling is indicated by the determined context information.

According to a second aspect of the invention, there is provided a computer program product having computer readable code embodied therein, the computer readable code being configured such that, on execution by a suitable computer or processing unit, the computer or processing unit performs the method as described above.

According to a third aspect of the invention, there is provided a fall detection system for use in detecting falls by a user, the fall detection system comprising a processing unit configured to determine context information about the user and/or the environment in which the user is located, and to increase the sensitivity of a fall detection algorithm used to detect falls by a user in the event that the determined context information indicates that the user is or may be at an increased risk of falling, the increase in sensitivity occurring while the increased risk of falling is indicated by the determined context information.

In some embodiments the context information comprises an indication of whether the user is performing a fall risk assessment test or balance training; and the processing unit is configured to determine that the user is or may be at an increased risk of falling if the context information indicates that the user is performing a fall risk assessment test or balance training.

In some embodiments the context information comprises an indication of whether the user is walking, and the processing unit is configured to determine that the user is or may be at an increased risk of falling if the context information indicates that the user is walking.

In some embodiments the context information comprises an indication of whether an unusual movement pattern for the user has been detected, and the processing unit is configured to determine that the user is or may be at an increased risk of falling if the context information indicates an unusual movement pattern.

In some embodiments the context information comprises an indication of the current location of the user, and the processing unit is configured to determine that the user is or may be at increased risk of falling if the current location of the user is a known location where the user is at a higher risk of falling. The known locations where the user is at a higher risk of falling may include any one or more of, a bathroom, on the stairs, outdoors or a location where the user and/or other users have previously fallen.

In some embodiments the context information about the environment in which the user is located comprises an indication of the ambient light in the user's location, an indication of how even or uneven the ground is, an indication of the current weather or temperature and/or an indication of the ambient noise level and the processing unit is configured to determine that the user is or may be at increased risk of falling if the ambient light is below a threshold, if the ground is uneven, if the weather is wet or the temperature is below a threshold and/or if ambient noise level is above threshold.

In some embodiments the context information comprises an indication of the current time, and the processing unit is configured to determine that the user is or may be at increased risk of falling if the current time is within one or more specified time periods. The one or more specified time periods may include the night time and/or time periods shortly before and/or after a scheduled dose of medication.

In some embodiments, the context information comprises an indication of the current activity level of the user, and the context information indicates that the user is or may be at increased risk of falling if the current activity level is above a threshold activity level.

In some embodiments, the processing unit is configured to increase the sensitivity of a fall detection algorithm to increase the likelihood that a fall will be detected.

In some embodiments, the processing unit is configured to increase the sensitivity of a fall detection algorithm by adjusting the position of an operating point for the algorithm on a receiver operating characteristic curve.

In some embodiments, the processing unit is configured to increase the sensitivity of the fall detection algorithm by decreasing the threshold at which the likelihood for a fall has to outweigh the likelihood for a non-fall for a fall to be detected.

In other embodiments, the processing unit is configured to increase the sensitivity of a fall detection algorithm by determining a required operating point for the algorithm on a receiver operating characteristic curve, and selecting a configuration of the fall detection algorithm having the required operating point.

In other embodiments, the fall detection algorithm comprises determining one or more feature values from measurements of the movements of the user and comparing the one or more feature values to respective thresholds to detect if a fall has occurred, and the processing unit is configured to increase the sensitivity of the fall detection algorithm by adjusting one or more of the thresholds to increase the likelihood that a fall will be detected.

In other embodiments, the fall detection algorithm comprises determining a plurality of feature values from measurements of the movements of the user; and comparing the set of feature values to a threshold to detect if a fall has occurred, and the processing unit is configured to increase the sensitivity of the fall detection algorithm by adjusting the threshold to increase the likelihood that a fall will be detected.

In other embodiments, the fall detection algorithm comprises determining one or more feature values from measurements of the movements of the user, determining a value indicating the likelihood that the set of feature values represents a fall and a value indicating the likelihood that the set of feature values does not represent a fall, determining a ratio of the likelihood values and comparing the logarithm of the ratio to a threshold to detect if a fall has occurred, and the processing unit is configured to increase the sensitivity of the fall detection algorithm by adjusting the threshold to increase the likelihood that a fall will be detected.

In some embodiments, the fall detection algorithm comprises determining one or more feature values from measurements of the movements of the user in two or more stages, with each stage only being performed if the feature value or values determined in the previous stage indicate that a fall may have occurred, and the processing unit is configured to increase the sensitivity of the fall detection algorithm by changing the feature value or values determined in one or more stages, and/or adjusting one or more threshold values to which the feature values are compared.

In some embodiments, the processing unit is further configured to determine further context information about the user and/or the environment in which the user is located; and to reset or reduce the sensitivity of the fall detection algorithm if the further context information indicates that the user is no longer at an increased risk of falling.

In some embodiments, the processing unit is configured to initially operate the fall detection system with the fall detection algorithm set to a normal sensitivity corresponding to a normal risk of falling for the user; and wherein when the processing unit determines that the context information indicates that the user is or may be at an increased risk of falling relative to the normal risk of falling for the user, the processing unit is configured to increase the sensitivity of the fall detection algorithm above the normal sensitivity.

In some embodiments, the processing unit is further configured to determine if the context information indicates that the user is or may be at a decreased risk of falling, and to decrease the sensitivity of the fall detection algorithm while the decreased risk of falling is indicated by the determined context information.

BRIEF DESCRIPTION OF THE DRAWINGS

Exemplary embodiments of the invention will now be described, by way of example only, with reference to the following drawings, in which.

DETAILED DESCRIPTION OF THE PREFERRED EMBODIMENTS

Figure 5:
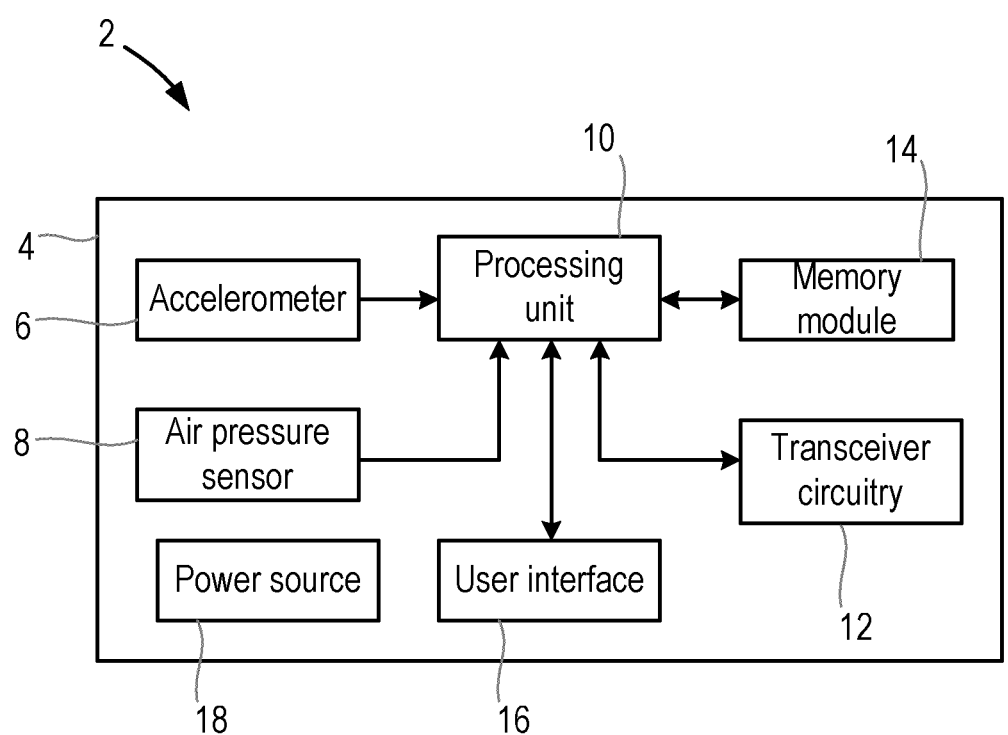
FIG. 5 is a block diagram of a fall detection system according to an embodiment of the invention.

A fall detection system 2 according to an embodiment of the invention is shown in FIG. 5. In this embodiment of the invention, the fall detection system 2 comprises a user device 4 that is designed to be worn or carried by a user.

The user device 4 is preferably in the form of a pendant that is worn on a cord or chain around the user's neck, but it will be appreciated that the user device 4 is not limited to this form factor, and it is possible that the user device 4 could instead be designed to be worn at the user's wrist or waist, on their chest or back, or carried in their pocket.

The user device 4 comprises one or more movement sensors for obtaining measurements of the movements of the user. The one or more movement sensors 6, 8 typically includes at least an accelerometer 6 for measuring the accelerations experienced by the user, and in this exemplary embodiment, the user device 4 also comprises an air pressure sensor 8 that obtains measurements of air pressure that can be processed to determine the height (altitude) or change in height of the user. The one or more movement sensors 6, 8 are connected to a processing unit 10. The processing unit 10 receives measurements from the movement sensors 6, 8, and processes the measurements to determine if the user of the fall detection system 2 has suffered a fall. The processing unit 10 also controls the operation of the user device 4.

It will be appreciated that the accelerometer 6 measures the accelerations experienced by the user device 4, and the processing unit 10 can analyse the accelerations to identify impacts, determine the speed, change in orientation and/or change in position or height of the user device 4. In certain embodiments, the processing unit 10 can also process the signal from the accelerometer 6 to detect the performance of predetermined gestures (i.e. movements) by the user with the user device 4 (for example shaking the user device 4, moving it in an oscillating motion, a circle, Fig. of 8, etc.). The signal from the air pressure sensor can be analysed by the processing unit 10 to determine the height and/or change in height of the user device 4.

It will be appreciated that although two movement sensors are shown in this embodiment, fall detection systems according to alternative embodiments may comprise only one movement sensor (for example just the accelerometer 6 with the air pressure sensor 8 being omitted). In yet further embodiments, the user device 4 can comprise a gyroscope and/or magnetic field sensor(s) in addition or alternatively to the air pressure sensor 8.

The user device 4 also comprises transmitter or transceiver circuitry 12 that allows the user device 4 to transmit an alarm signal to a remote call centre or the emergency services in the event a fall is detected. The transmitter or transceiver circuitry 12 can be configured to communicate with a base station associated with the user device 4 (which can then issue an alarm or summon help from a healthcare provider or the emergency services) or via a public telephone network (such as a mobile telecommunications network) to a remote station (for example located in call centre of a healthcare provider). Where the transmitter or transceiver circuitry 12 is configured to communicate with a base station, the circuitry 12 may be configured according to any known wireless technology, for example Wi-Fi, Bluetooth, Zigbee, Near Field Communication (NFC), etc. Where the transmitter or transceiver circuitry 12 is also or alternatively provided to enable communications with a public telephone network, such as a mobile telephone network, the circuitry 12 may be also or alternatively configured for use with any suitable type of second-, third- or fourth-generation communication network, including GSM, WCDMA, LTE, etc. Also, although not shown in FIG. 5, the user device 4 may comprise a loudspeaker and/or microphone for enabling a user to communicate with the healthcare provider or the emergency services.

The user device 4 also comprises a memory module 14 that is connected to the processing unit 10 and that can store measurement data from the movement sensors 6, 8, and/or computer readable code for use by the processing unit 10.

It will be appreciated that the memory module 14 may only store the latest measurement data or the measurement data from predefined periods of time.

Optionally, the user device 4 can include a user interface 16 that provides information to the user and/or allows the user to interact or control the user device 4. The user interface 16 can comprise user input components, such as buttons, keys, switches, trackballs, touch screens or a microphone; and/or user feedback components, such as a speaker, lights, LEDs, a display or a vibration device (for providing tactile feedback to the user). In some embodiments, the user interface 16 comprises at least a dedicated button for the user to press to request help in an emergency (this button is sometimes known as a personal help button).

The user device 4 also comprises a power source 18, such as a battery that provides power to the components of the user device 4.

Figure 1:
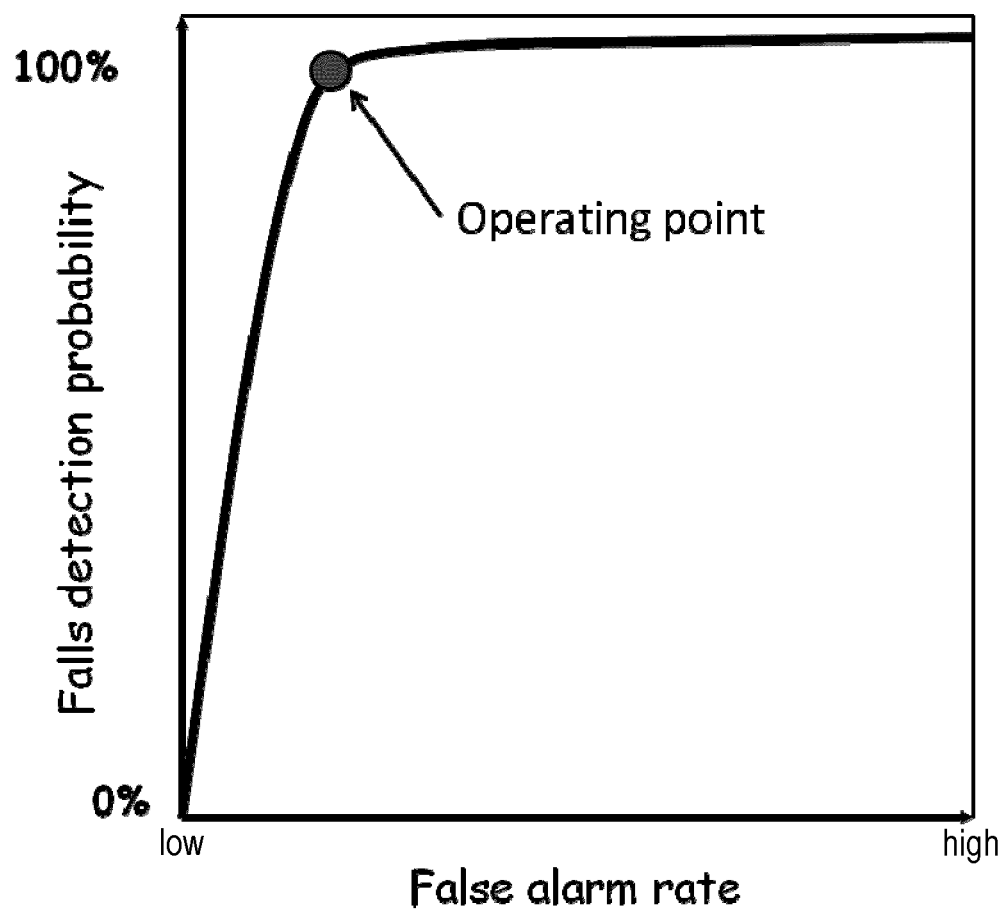
FIG. 1 is a graph illustrating an exemplary ROC curve for a fall detection algorithm.
Figure 2:
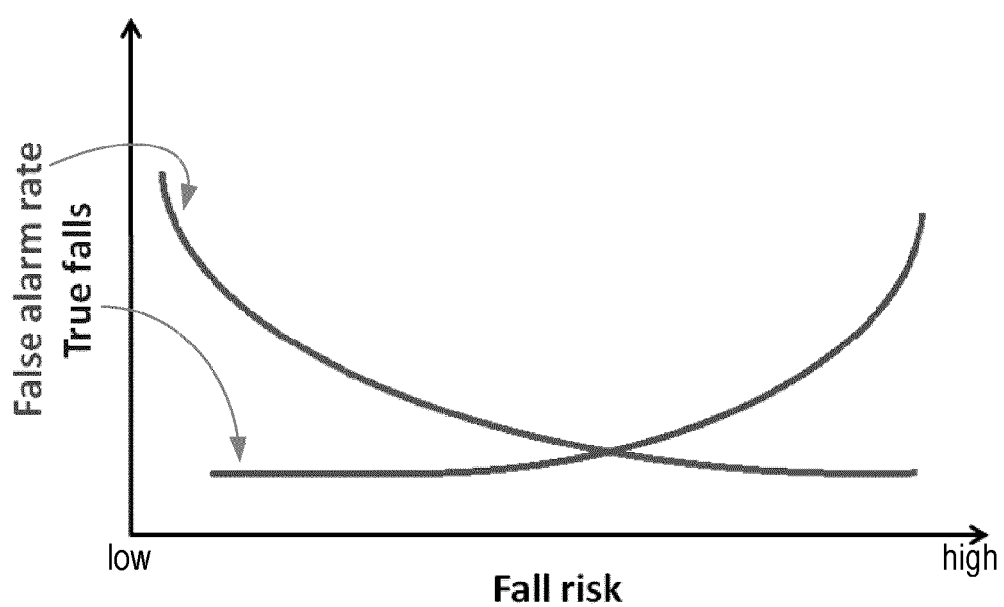
FIG. 2 is a graph illustrating the false alarm rate and the true fall rate against a user's fall risk.
Figure 3:
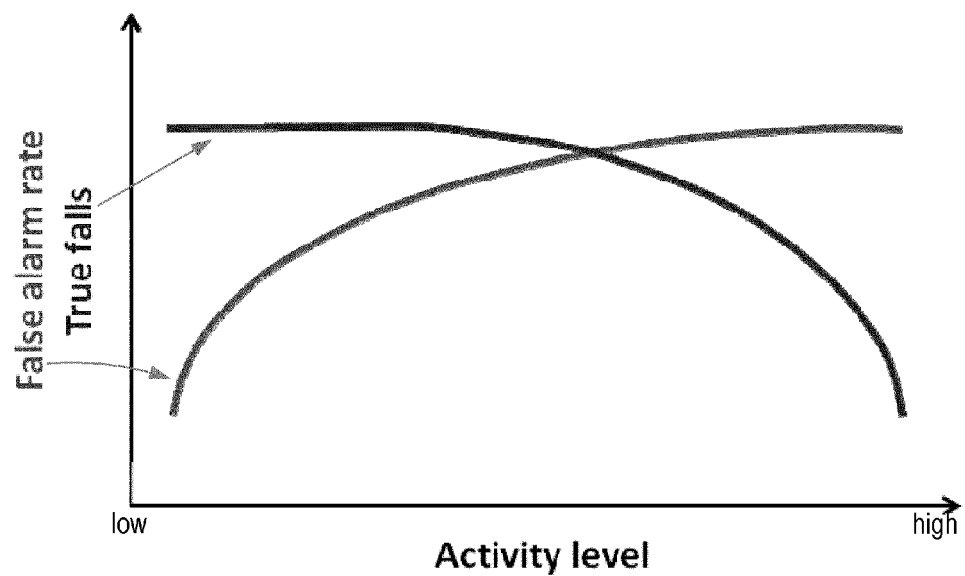
FIG. 3 is a graph illustrating the false alarm rate and the true fall rate against a user's activity level.
Figure 4:
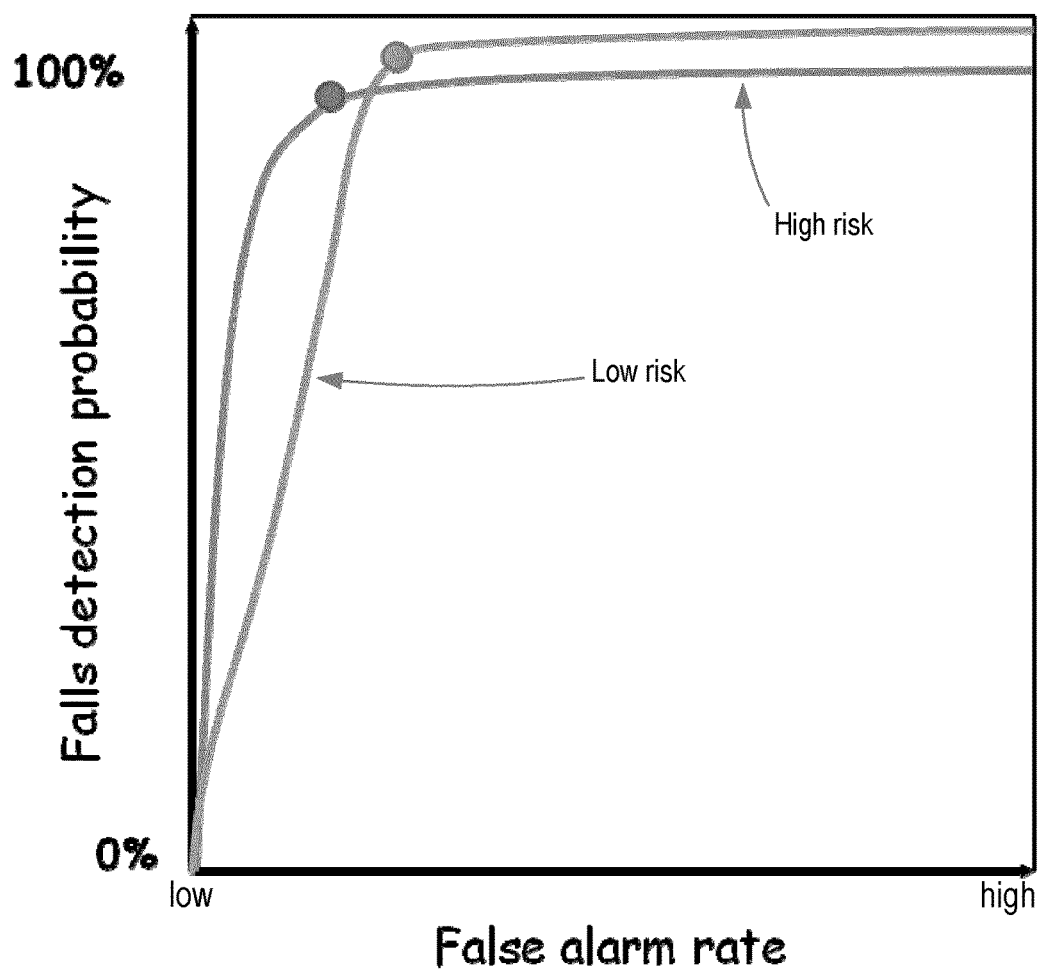
FIG. 4 is a graph illustrating two exemplary ROC curves for users with high and low fall risks respectively.

In alternative embodiments to that shown in FIG. 1, the fall detection system 2 can further comprise a base unit that can be located in the home of the user and that communicates wirelessly with the user device 4. The base unit may also act as a charging station for the user device 4. The base unit may comprise circuitry for enabling communications between the user and a remote call centre (such as the emergency services) via a public switched telephone network and/or a mobile communications network, and/or may provide a connection to the Internet. In some implementations of this system 2, the processing and operations according to the invention can be performed by the processing unit 10 in the user device 4, with the base unit being provided merely to facilitate communications with the remote call centre/emergency services/Internet. In alternative implementations, the user device 4 can communicate the measurements obtained by the movement sensors 6, 8 to the base unit, and a processing unit in the base unit can perform the processing and operations according to the invention using the measurements. This latter embodiment has the advantage that the power consumption of the user device 4 can be substantially reduced.

In yet further embodiments, the user device 4 of the fall detection system 2 can be configured to connect to another electronic device belonging to the user, such as a computer, laptop, tablet or smartphone, to enable the user to control the user device 4 via that electronic device. In these embodiments, the connection can be established using any known wireless technology, for example Wi-Fi, Bluetooth, Zigbee, Near Field Communication (NFC), etc. In these embodiments, the use of another electronic device to control the user device 4 can replace the need for a user interface 16 to be included in the user device 4 (apart from perhaps a single personal help button). In these embodiments, the other electronic device could also be used to process the movement measurements to detect a fall rather than the user device 4 to reduce the power consumption of the user device 4.

In some embodiments, a remotely-located clinician or other healthcare provider can interact with the user via the user device 4. For example, the clinician or healthcare provider may contact the user via the transceiver circuitry 12 in the user device 4 and advise the user they should perform a fall risk assessment or take some medication.

In some implementations the processing unit 10 in the user device 4 determines if the user has suffered a fall using a fall detection algorithm by extracting values for a feature or various features that are associated with a fall from the movement sensor measurements. For example, the accelerations and air pressure changes experienced by the user device 4 are measured using the accelerometer 6 and air pressure sensor 8, and these measurements are analysed by the processing unit 10 to determine whether the user has suffered a fall.

A fall can be broadly characterised by, for example, a change in altitude of around 0.5 to 1.5 meters (the range may be different depending on the part of the body that the user device 4 is to be worn and the height of the user), culminating in a significant impact, followed by a period in which the user does not move very much. Thus, in order to determine if a fall has taken place, the processing unit 10 can process the sensor measurements to extract values for features including one or more of a change in altitude (which can be derived from the measurements from the air pressure sensor 8, but can also or alternatively be derived from the measurements from the accelerometer 6, for example if the air pressure sensor 8 is not present), a maximum activity level (i.e. an impact) around the time that the change in altitude occurs (typically derived from the measurements from the accelerometer 6) and a period in which the user is relatively inactive following the impact (again typically derived from the measurements from the accelerometer 6). It will be appreciated that other features can further improve the detection algorithm. For example, the detection of a change in orientation upon falling can improve the likelihood that the signal is due to a fall.

A fall by the user can be identified where a subset or all of the above features are identified in the measurements. In other words, a fall may be identified where any one or more of the required height change, impact and inactivity period are detected in the measurements.

As discussed below, the fall detection system 2 uses a fall detection algorithm that processes the features (e.g., height change, impact, orientation, etc.) derived from the measurements from the movement sensor(s) 6, 8 to determine if the user has fallen. In some embodiments, when full fall detection processing is carried out, it is determined whether the set of feature values is in a (multidimensional) region corresponding to a fall. Preferably, a value indicating the likelihood of a fall is determined for the set of feature values, and this likelihood is compared to a threshold to determine if a fall has occurred. Alternatively, each individual feature value can be compared to a respective threshold, and a fall detected if a certain number of features exceed their threshold value.

In another (preferred) alternative, the fall detection algorithm can be executed in stages, with the movement sensor measurements being continuously evaluated by a light-weight (in processing terms) algorithm in a first stage to detect a potential fall incident (with a potential fall being indicated, for example, by an impact of sufficient magnitude being detected or a change in height downwards greater than a predetermined amount). If a potential fall incident is detected, a 'trigger' is generated. If a trigger is generated, the movement sensor measurements around the time instant in the measurements that the trigger was found are evaluated in the second stage. In this stage several features are computed. For example, height change, orientation change, vertical velocity, and impact can be computed. Each of these feature values may be compared to a threshold, and if the comparison of the feature values to the thresholds is not consistent with a fall, then the second stage fall detection processing is stopped and light-weight processing of the movement sensor measurements is resumed.

If the comparison of the feature values to the thresholds is consistent with a fall (or if there is no comparison of the feature values to thresholds at this stage, a third processing stage is entered. In this third stage, the computed feature values are evaluated by a classifier, for example a Naive Bayesian Classifier (NBC). The classifier has been trained on general population fall data and/or user specific fall and activity data. This third stage can be seen as a (second) thresholding test—with the difference from the second stage being that the set of feature values is compared to a single threshold rather than comparing the feature values to respective thresholds. Since the classifier outcome is binary (i.e. a fall or non-fall), it is usually called a detector. If a fall is detected, a fourth optional stage can be entered, e.g. in which a decision can be made as to whether to revoke a fall alarm or to test the feature set for exceptional situations such as an accidental drop of the device (in some cases the exceptions might also be tested in an earlier stage in the sequence, preceding the second or third stage).

The behaviour of the overall fall detection algorithm (or just the third stage alone) can be evaluated through a ROC curve. A likelihood can be assigned to the set of feature values representing how likely it is that the set of values corresponds to a fall. Likewise, a likelihood can be assigned to the set representing how likely it is that the set of values corresponds to a non-fall (it should be noted that these two likelihoods are not complementary, i.e. they do not necessarily sum to 1). The ratio of the two likelihoods is the likelihood ratio, the logarithm of which is known as the log likelihood ratio (LLR).

In the third processing stage described above, the classification (detection of a fall) comprises comparing the LLR for the set of feature values to a threshold. If the threshold is exceeded a fall is detected, otherwise the event is classified as a non-fall. A low threshold will make detection of falls more likely (corresponding to a fall detection algorithm with high or higher sensitivity), however at the cost of an increased rate of false alarms (low specificity). A high threshold will raise the specificity, however at the cost of missing falls (corresponding to a fall detection algorithm with reduced sensitivity). The ROC curve plots these numbers against each other, where the threshold is varied as a parameter.

It will be noted from the discussion in the Summary section above that it is not possible to configure the fall detection algorithm to operate at an optimum point on the ROC curve for all users and in all situations, so the invention provides that the sensitivity of the fall detection algorithm is adapted using contextual information about the user and/or the user's environment.

The fall detection algorithm will have a default or normal sensitivity level (i.e. a default or normal point on the ROC curve) that may be common to all users, or a default or normal sensitivity level that is specific to the user, which can be calibrated to the user based on fall risk assessments performed by the user when the system 2 is first set up and/or on user characteristics, and/or which can be adjusted over the long term based on repeated fall risk assessments. The default or normal sensitivity level is the sensitivity level used when the user is at their default or normal risk of falling.

In accordance with the invention, where the contextual information about the user and/or the user's environment indicates that the user is temporarily at an increased risk of falling (i.e. relative to the normal risk of falling for the user), the sensitivity of the fall detection algorithm is increased to improve the chances of a fall by the user being detected. In some embodiments, the contextual information about the user and/or the user's environment can be further examined to determine if the user is temporarily at a reduced risk of falling (i.e. relative to the normal risk of falling for the user) or if the user is engaging in an activity that is more likely to generate false alarms, in which case the sensitivity of the fall detection algorithm can be temporarily reduced to decrease the chance of a false alarm being issued.

Figure 6:
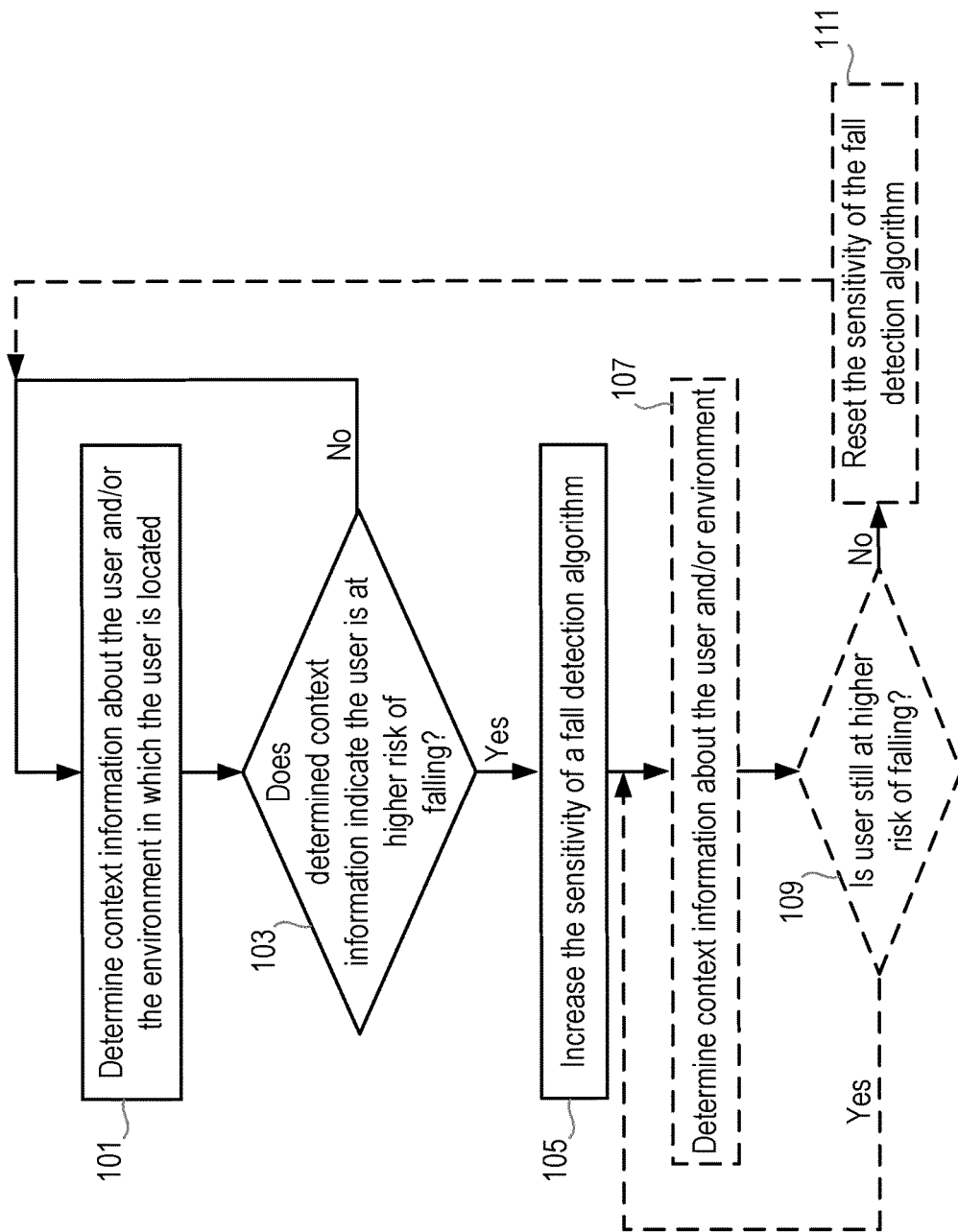
FIG. 6 is a flow chart illustrating a method according to an embodiment of the invention.
Figure 7:
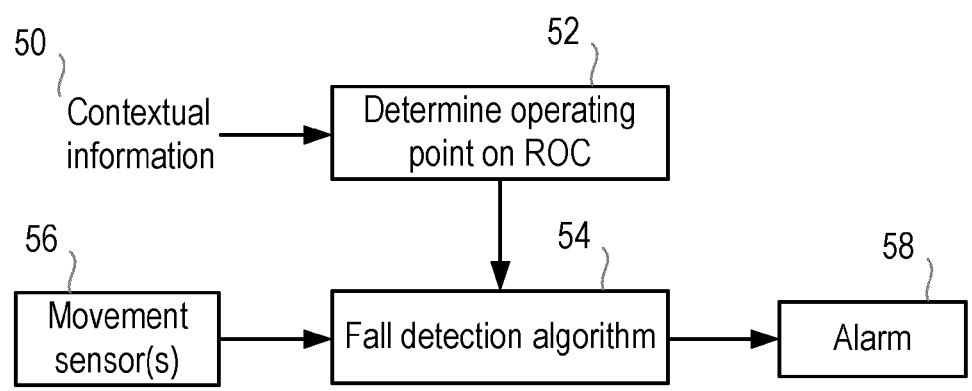
FIG. 7 is a functional flow chart illustrating the operation of an embodiment of the invention.

The flow chart in FIG. 6 illustrates an exemplary method of operating a fall detection system according to the invention in which the sensitivity of the fall detection algorithm is increased while the contextual information indicates that the user is at an increased risk of falling. Those skilled in the art will appreciate that similar steps can be used in the further embodiments where the sensitivity of the fall detection algorithm is reduced if the contextual information indicates that the user is at a lower risk of falling. FIG. 7 is a functional block diagram illustrating the operation of the invention according to an exemplary embodiment. It will be appreciated that while the method of FIG. 6 is being performed, the fall detection system 2 is measuring the movements of the user from the movement sensors 56 and continuously or periodically processing them using the fall detection algorithm 54 to determine if the user has fallen.

In step 101, context information about the user and/or their environment is determined by the processing unit 10. The way in which the context information is determined depends on the particular type of context information and will be briefly described below. The context information can comprise any one or more of: an indication of whether the user is performing a fall risk assessment test or balance training, an indication of whether the user is walking, an indication of whether an unusual movement pattern for the user has been detected, information indicating the location of the user, information on the environment around the user, an indication of the current time and/or an indication of the activity level of the user (which can comprise the activity level of the user at that time point or the activity profile over a period of time, such as an hour or day).

In step 103, it is determined whether the context information indicates that the user is currently at a higher risk of falling. If the context information does not indicate that the user is at a higher risk of falling, then the method returns to step 101 and further/new context information is determined.

If any of the context information indicates that the user is currently at a higher risk of falling, the sensitivity of the fall detection algorithm (represented by block 54 of FIG. 7) is increased in order to reduce the chances of a fall not being detected. The way in which the sensitivity of the fall detection algorithm is increased depends on the nature of the fall detection algorithm being used. Where each of the derived feature values are compared to respective thresholds, increasing the sensitivity of the algorithm can comprise adjusting one or more of the thresholds to make a positive fall indication more likely. Where the set of feature values is compared to a threshold, or a likelihood value for the set of feature values is compared to a threshold, increasing the sensitivity of the algorithm can comprise adjusting the threshold value to make detection of falls more likely (i.e. reducing the threshold if a likelihood value over the threshold indicates a fall). Where a LLR is derived and compared to a threshold value, adjusting the sensitivity of the algorithm comprises adjusting the operating point on the ROC curve (resulting in the use of a different (lower) threshold value. Alternatively, the memory module 14 can store different configurations of the fall detection algorithm with each configuration having a known position on the ROC curve, and step 105 can comprise determining a required operating point on the ROC curve and selecting the appropriate fall detection algorithm to use. Alternatively, where the fall detection algorithm is in the form of a state machine, increasing the sensitivity of the fall detection algorithm can comprise using a different feature in the first (trigger) stage, and/or adjusting the threshold that the trigger feature is compared to, and/or adjusting the thresholds used in the second stage.

The increase in the sensitivity of the fall detection algorithm in step 105 is preferably temporary and only lasts while the user is at the higher risk of falling. Once the user's risk of falling returns to a normal level (for the user or for an average user) or a default level, the sensitivity of the fall detection algorithm is reset to the previous sensitivity level. In alternative implementations, the sensitivity of the fall detection algorithm can be returned to near its previous sensitivity. This is illustrated in steps 107-111 of FIG. 6.

Thus, in step 107, further context information about the user and/or the user's environment is determined. This context information is determined in the same way as in step 101. In some cases, step 107 can comprise monitoring for changes in the context information.

In step 109 it is determined from the context information determined in step 107 whether the user is still at a higher risk of falling. If the user is still at the higher risk of falling, the method returns to step 107 and further context information is determined.

If the context information indicates that the user is no longer at a higher risk of falling, the method moves to step 111 in which the sensitivity of the fall detection algorithm is reset back to the original sensitivity (i.e. the sensitivity used prior to step 105). The method then returns to step 101.

The processing performed in steps 103-111 is represented by functional block 52 in FIG. 7. Following execution of the fall detection algorithm 54, an alarm 58 can be triggered if a fall is detected.

It will be appreciated that in some implementations, the operations of multiple steps in FIG. 6 can be combined into a single step. For example, steps 101 and 107 can be combined, steps 103 and 109 can be combined and/or steps 105 and 111 can be combined.

Figure 8:
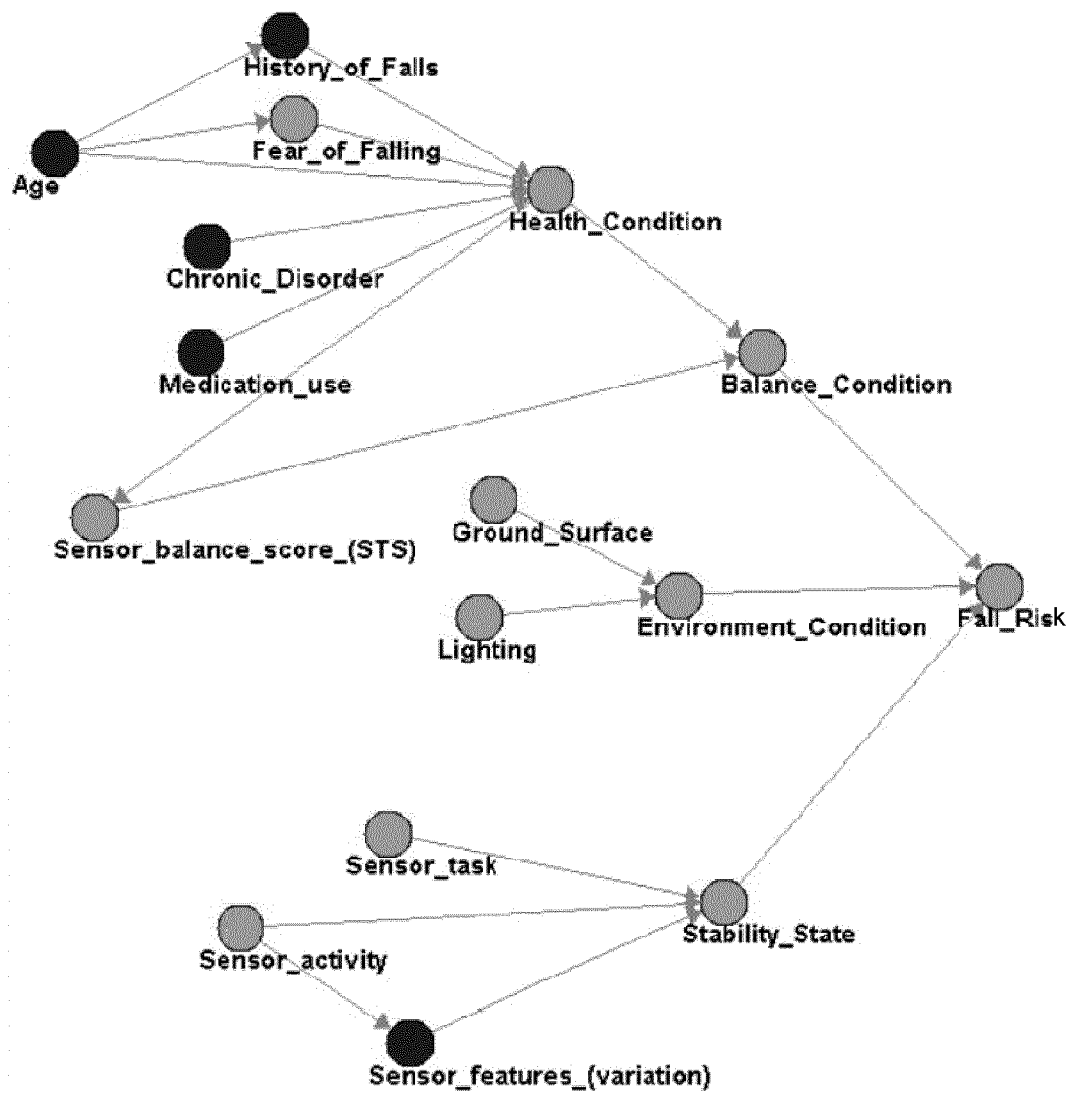
FIG. 8 is an example of a Bayesian network applied to fall risk estimation.

It will be appreciated that steps 103 and 105 can comprise processing the determined context information to modify the ROC-curve using a Bayesian network. An exemplary Bayesian network is shown in FIG. 8. The network includes different nodes, each representing a different risk factor. All nodes contribute to the root node, which holds the fall risk. There are different types of risks. These are reflected in the hierarchy of the tree. In this exemplary figure, three main classes can be seen to be modelled. They are sensor data obtained from observing the user, short term context information like current lighting conditions, and long term health conditions like chronic diseases and history of falls. The arrows in the network hold the conditional probabilities for the values of the arriving node given the value(s) of the departing node(s). In this way, the probability of the fall risk is expressed by the joint of the factors represented by the other nodes. The leaf nodes are assigned with a default value, which is the prior probability (the most commonly encountered value for this population in practice). When the value is known, this is assigned to the node replacing the default. It can also happen that the value of an intermediate node is known. Then this value is assigned (as well). As a consequence of such a value change, the value at the other nodes will also change. This update happens according to the given conditional probabilities. Efficient algorithms to perform the updating are known in the art. As is also known in the art, a Bayesian Network can advantageously be designed with the arrows in opposite direction, i.e. reversing the "cause" and "effect" nature of the nodes. This helps to reduce the complexity of the network (leading to faster updating) as well as helping to arrive at the prior and conditional probability values.

In some embodiments, the user will have a certain fall risk for the common, daily situation. When the user engages in an exercise to improve their balance, for example, the corresponding node (not present in the figure, but similar to the "lighting conditions" one) would be assigned another value, and the effect will propagate to the fall_risk node, which in turn would drive the output 54 in FIG. 7, possibly after some additional processing to convert the fall_risk value into a ROC operating point (e.g. LLR threshold). As explained above, the detection of "engaging in exercise" may also immediately drive output 54. The Bayesian Network can be advantageous if, for example, in addition to the changing context node, other additional nodes modify, e.g. during part of the exercising.

As noted above, in exemplary embodiments, the context information determined in step 101 can comprise any one or more of: an indication of whether the user is performing a fall risk assessment test or balance training, an indication of whether the user is walking, an indication of whether an unusual movement pattern for the user has been detected, information indicating the location of the user, information on the environment around the user, an indication of the current time and/or an indication of the activity level of the user.

Where the context information comprises an indication of whether the user is performing a fall risk assessment test or balance training, the fall detection system 2 can determine this context information in a number of different ways. For example, a user may interact with the system 2 at the start of the assessment test or balance training to indicate that a test or training is to start (this may particularly be the case where the fall detection system 2 is also used as part of the assessment test or to monitor the balance training. The interaction may comprise the user performing a predefined gesture with the user device 4, pressing a button on the user device 4, or selecting an option within a menu-based user interface. Alternatively, a care provider for the user can provide an input or signal to the system 2 indicating that the assessment test or training is to start. In some cases, the assessment test or balance training may take a preconfigured amount of time (in which case the end point is known), but in other cases the user or care provider can perform another interaction with the system 2 to indicate that the test or training is complete. Alternatively, the completion of the test or training can be detected from processing of the measurements from the movement sensors. It will be appreciated that when a user is performing a fall risk assessment test, balance training or other exercises, their physical abilities are being tested and pushed close to their limits, which puts the user at a higher risk of falling during the test or training Thus, when the context information determined in step 101 indicates that the user is performing a fall risk assessment test or balance training or other exercises, it is determined in step 103 that the user is at a higher risk of falling and the sensitivity of the fall detection algorithm is increased in step 105. Once the context information indicates that the user has completed or otherwise finished the test or training, the sensitivity of the fall detection algorithm can be reduced or reset to the previous setting.

Where the context information comprises an indication that the user is walking, the processing unit 10 can determine whether the user is walking by processing the measurements from the movement sensors 6, 8 to identify a pattern consistent with walking (such as regular heel-strikes, etc). Techniques for processing movement sensor measurements to identify walking patterns are known in the art and will not be described further herein. Alternatively or in addition, if the fall detection system 2 includes some form of location tracking function (for example a satellite positioning system receiver), an indication that the user is walking can be inferred from changes in the location of the user over time. Walking increases the risk of falling for a user, and therefore when the context information indicates that the user is walking, the user is deemed to be at a higher risk of falling (step 103) and therefore the sensitivity of the fall detection algorithm is increased while the user is determined to be walking. If the processing unit 10 determines that the user is no longer walking, the user's fall risk is therefore lower and the sensitivity of the fall detection algorithm can be reduced or reset to the previous setting.

Where the context information comprises an indication of whether an unusual movement pattern for the user has been detected, the processing unit 10 can determine this by processing the measurements from the movement sensors 6, 8. Unusual movement patterns can be movement patterns outside the normal range of movements for a user, which may result from the user entering a new or physically challenging environment (e.g. walking up a hill or on uneven ground). Unusual movement patterns outside the normal range could include movements such as slips and trips by the user. It has been shown that mis-steps (including near falls or trips and slips) are more prevalent than falls and it has been suggested that near falls could be a valid proxy for fall risk (Srygley, J. M., T. Herman, et al. (2009). "Self-report of missteps in older adults: a valid proxy of fall risk?" Archives of Physical Medicine and Rehabilitation 90(5): 786-792.). Machine learning algorithms can be used to learn the typical movement characteristics of an individual user. Disturbances on these characteristic movements (i.e. movement patterns outside the normal range) can be quantified in order to identify near falls. Unusual movement patterns outside the normal range can also occur when walking quicker than normal (e.g. when the user is rushing to catch a bus), when walking the dog (for example if the dog suddenly pulls on the lead). Unusual movement patterns might also include picking up an object from the ground if this movement is infrequently performed by that user. In some implementations, an unusual movement pattern can be any movement or activity that the user rarely or never performs in their daily routine. During an unusual movement pattern the user is considered to be at a higher risk of falling, and therefore the sensitivity of the fall detection algorithm is increased. Once the processing unit 10 determines that the unusual movement patterns are no longer present in the user's movements (i.e. the user is no longer performing the unusual movement pattern), the sensitivity of the fall detection algorithm can be reduced or reset to the previous setting.

Where the context information comprises information indicating the location of the user, this information can be provided by a location tracking function in the fall detection system 2, such as a satellite positioning system receiver and/or an indoor location tracking system. The processing unit 10 can interpret the location information provided by the receiver or indoor tracking system to determine some context for the location, such as the location is the user's home, a hospital, the shops, etc., and/or the part of their home the user is in, e.g. lounge, bathroom, stairs, etc. Alternatively or in addition, the processing unit 10 can determine if the location of the user coincides with a location in which the user or other users have previously fallen (with a match with one of those locations indicating that the user may be at a higher risk of falling). A user may be at a higher risk of falling when in unfamiliar locations (e.g. shops), when outdoors, and/or in particular parts of their house, e.g. in the bathroom (where it may be wet and slippery) or on the stairs, and therefore if the context information indicates that the user is at a known location where there is a higher risk of falling, the sensitivity of the fall detection algorithm will be increased while the user is at that location. When the user moves into a location where there is a lower or normal risk of falling, the sensitivity of the fall detection algorithm can be reduced or reset to the previous setting.

Where the context information comprises information on the environment around the user, this information can include any of an indication of the ambient light in the user's location (with low light levels leading to the user being at a higher risk of falling due to impaired visibility) which can be measured using a light sensor in the fall detection system 2, an indication of how even or uneven the ground is (including whether there is a slope or stairs), an indication of the current weather or temperature (e.g. with rain or icy conditions leading to the user being at a higher risk of falling), an indication of the ambient noise level (e.g. with higher ambient noise levels increasing the risk that the user can become disorientated or confused thus placing the user at a higher risk of falling), etc. If the context information on the environment around the user indicates that there is low lighting, the ground is uneven, it is raining or icy, and/or it is particularly noisy, then the user is at a higher risk of falling, and the sensitivity of the fall detection algorithm can be increased in step 105. If the context information subsequently indicates that there is good lighting in the environment, the ground is relatively even, it is no longer wet, raining or icy, and/or it is not particularly noisy, the sensitivity of the fall detection algorithm can be reduced or reset to the previous sensitivity.

Where the context information comprises an indication of the current time, this can be provided by an internal clock in the processing unit 10. The user may be at a higher risk of falling during certain times of the day, for example at night time or shortly before or after taking a scheduled dose of medication, and therefore step 103 can comprise comparing the current time to a predetermined medication schedule and/or to a range of times when the user is deemed to be at a higher risk of falling.

Where the context information comprises an indication of the activity level of the user, the processing unit 10 can determine the activity level from the measurements from the movement sensors 6, 8. Techniques for determining an activity level from movement sensor measurements are known in the art and will not be described in detail herein. The activity level can be determined for the user at that time point (i.e. when step 103 is performed) or an activity profile for a period of time, such as an hour or day, can be determined from the measurements from the movement sensors 6, 8. The user may be at a higher risk of falling when more active, so step 103 can comprise comparing the determined activity level to a threshold, and determining that the user is at a higher risk of falling if the activity level is above the threshold. In that case, the sensitivity of the fall detection algorithm can be increased while the user is particularly active. Once the user's activity level falls below the threshold, the sensitivity of the fall detection algorithm can be reduced or reset to the previous setting. In some embodiments, if an activity profile is determined, the activity profile can be compared to activity profiles determined for previous periods of time to determine if the user is more active than usual or fatigued (for example following a period of time in which the user has been more active than usual or otherwise particularly active), and if the comparison indicates that the user is more active than usual or fatigued, the sensitivity of the fall detection algorithm can be temporarily increased until the activity profile returns to the usual level.

In some embodiments, the context information can include or be an indication of the variability in the walking pattern of the user, since variability in the walking pattern can be affected by fatigue (as described in "Physical Fatigue Affects Gait Characteristics in Older Persons" by Helbostad et al., Journal of Gerontology: Medical Sciences, 2007, Vol 62A, No. 9, 1010-1015), with the sensitivity of the fall detection algorithm being increased if the context information indicates that the user is fatigued.

The context information can also or alternatively include other information about the user, such as an indication of whether the user is making use of a walking aid such as a walking stick or frame (if the user is typically required to use this type of walking aid), an indication of whether the user is wearing glasses (if the user should normally wear glasses), and/or an indication of the type of shoes the user is wearing. If the context information indicates that the user is not using a required walking aid, not wearing their glasses and/or not wearing their regular or the correct shoes the user's fall risk is increased and the sensitivity of the fall detection algorithm can be increased accordingly. Those skilled in the art will be aware of various techniques and sensors that can be used to determine if the user is making use of a walking aid, wearing their glasses or wearing the correct shoes.

In the embodiments where the sensitivity of the fall detection algorithm is reduced if the context information indicates that the user is temporarily at a lower risk of falling or if the user is engaging in an activity that is more likely to generate false alarms, such context information can indicate, for example, that the user is playing a sport or performing an activity where there are many bending, impact-like and/or ground touching movements (e.g. playing golf, gardening, etc.).

Figure 9:
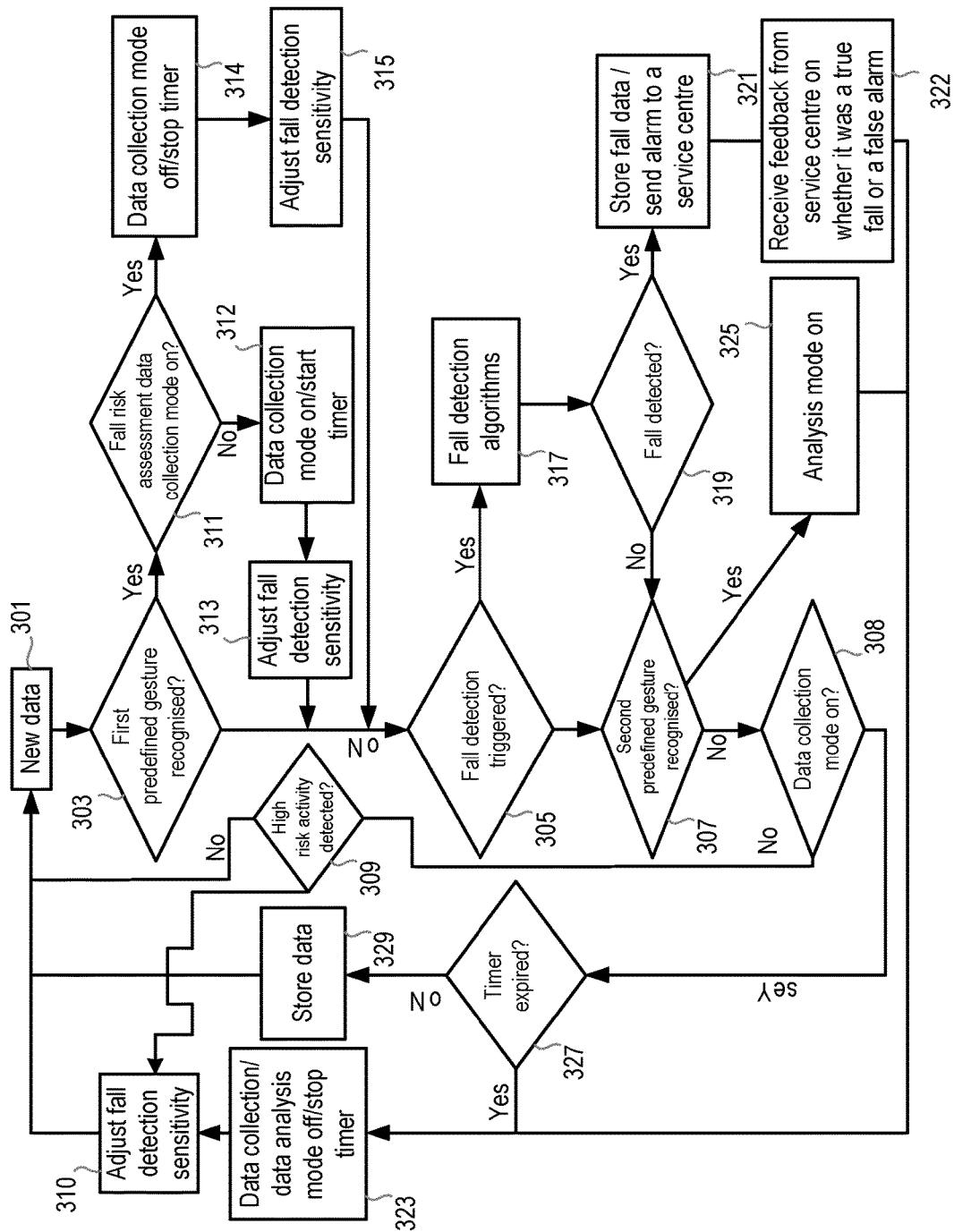
FIG. 9 is a flow chart illustrating the operation of the system according to a specific embodiment.

A specific embodiment of the invention is illustrated by the flow chart in FIG. 9. In this embodiment, the context information includes an indication of whether the user is performing a fall risk assessment test and whether the user is performing a high risk activity (e.g. walking, walking on uneven ground, walking up or down stairs, moving in the bathroom, etc.). In this embodiment the sensitivity of the fall detection algorithm is increased while the contextual information indicates that the user is at an increased risk of falling. Those skilled in the art will appreciate that a similar method can be used where the sensitivity of the fall detection algorithm is further to be reduced while the contextual information indicates that the user is at a lower risk of falling. In this embodiment the fall detection system 2 is also configured to conduct the fall risk assessment test and consequently the system 2 is configured to operate in three different modes. The first mode is a fall detection mode in which the system 2 processes the measurements from the movement sensors 6, 8 to detect a fall as described above. The second mode is a fall risk assessment data collection mode which is entered when the user starts the fall risk assessment (which in this embodiment is indicated to the system 2 by the user performing a predefined gesture with the user device 4, such as shaking the device 4, moving the device 4 in a predefined pattern, or pressing a button on the device 4) and in which the system 2 stores the measurements from the movement sensors 6, 8 in the memory module for subsequent analysis. During the fall risk assessment, the user performs certain movements and/or exercises for the purposes of assessing fall risk. The end of the fall risk assessment data collection mode can be indicated to the system 2 by the user (for example by performing another or the same predefined gesture with the user device 4 or by pressing the or another button), or the data collection mode can be ended after a predetermined time period. After completing the data collection mode, the system 2 returns to operating in the fall detection mode. The third mode is a fall risk data analysis mode in which the movements measured and stored during the fall risk assessment data collection mode are analysed to determine or estimate the fall risk for the user. The data analysis mode can be entered automatically on completion of the data collection mode, or it can be entered at a predetermined time or in response to an input from the user (for example as indicated by the user performing another gesture with the user device 4 or pressing another button). After completing the data analysis mode, the system 2 returns to operating in the fall detection mode.

While the user device 4 is operating in the data collection mode and storing the movement measurement data collected during the fall risk assessment and operating in the data analysis mode and determining the fall risk, the user device 4 is preferably still processing the measurements of the movement of the user in real-time or near real-time in order to determine if the user has fallen (the same as if the user device 4 was operating in the fall detection mode). If the fall detection system 2 detects a fall while in the data collection mode or data analysis mode, an alarm is triggered in the normal way (i.e. as if the system 2 was operating in the fall detection mode).

There are a number of different movement(s) and/or exercise(s) that the user could perform as part of a fall risk assessment. Each movement or exercise can test the user's walking ability, their balance, strength or reaction time, or any combination of these. Examples of suitable movement(s) and/or exercise(s) include the user standing still in various ways (e.g. feet together, near tandem, tandem, one leg, etc.), walking, a sit-to-stand transfer (i.e. standing up from a sitting position), a timed-up-and-go test (i.e. timing how long it takes the user to stand up, walk a certain distance and then return to a sitting position on the chair), and a reaction test involving timing how long it takes the user to react to a visual and/or audible stimulus from the user device 4, picking up an object from a low level (e.g. the floor), or turning around some predetermined angle (e.g. 360 degrees). Each of these movements or exercises can be performed by the user with different levels of difficulty to provide a better indication of the fall risk of the user. These movements and exercises are also typically included as part of a fall prevention exercise program to help the user reduce their risk of falling over time.

The use of these movement(s) and/or exercise(s) in assessing fall risk are known in the art, as are techniques for identifying them in measurements of the movement of a user and for analysing how well the user has performed them, so detailed techniques for processing the movement measurements are not provided herein.

A more detailed method of operating a user device 4 according to an embodiment of the invention is shown in FIG. 7. In this embodiment, the fall detection mode comprises two levels of processing. In a first, low power stage, the processing unit 10 analyses the measured accelerations for a single easily-detected characteristic of a fall, such as an impact (e.g. an acceleration greater than a threshold value). This low-power processing can be performed for each new block of measurement data. If at any time the characteristic is detected, the processing unit 10 activates the full fall detection processing and the measurements are processed to detect whether other characteristics of a fall are present, such as a free-fall, height change, change in orientation, etc.

In FIG. 9, the system 2 starts in the fall detection mode with a standard sensitivity for the fall detection algorithm. The fall detection algorithm comprises a low-power initial processing stage that looks for a trigger feature in the movement sensor data and a full processing stage that is activated when the trigger feature is found.

For each block of new measurement data (301) the processing unit 10 checks if a first predefined gesture is recognized (e.g. turning the device 4 to start or stop the data collection mode) (303). If the first predefined gesture is not recognized, the processing unit 10 checks if the fall detection algorithm should be triggered (305) (i.e. through processing of the movement data). If not, the processing unit 10 checks whether a second predefined gesture used to start the data analysis mode is recognized (e.g. shaking the device 4) (307). If not, the processing unit 10 checks if the device 4 is already in the fall risk assessment data collection mode (308). If not, the user device 4 continues operating in the fall detection mode (and in particular using the low-power processing of the measurement data), meaning that no data is stored in the user device 4, no timers are running, and the full fall detection algorithm is not running and no stored data is being analysed to determine fall risk.

At this stage it is also checked whether the context information indicates that the user is performing a high risk activity (309). If not, the processing unit 10 returns to 301 and operates on the next block of measurement data. If the context information indicates that the user is performing a high risk activity, the method moves to 310 in which the sensitivity of the fall detection algorithm is increased. The increased sensitivity fall detection algorithm is then used to process the next and subsequent blocks of measurement data 301 until the context information indicates that the user is no longer at an elevated risk of falling.

It will be appreciated that the checks in 303 (for the first predefined gesture being performed), 305 (for the fall detection being triggered) and 307 (for the second predefined gesture being performed) can be performed in a different order to that shown in FIG. 9. It will also be appreciated that the checks can be performed at the same time rather than in series.

If at 303 the first predefined gesture is recognized, the user device 4 checks whether the device 4 is already operating in the fall risk assessment data collection mode (311). If not, the data collection mode is started and a timer started (312). During the data collection mode data is stored and the timer is running. As the user is now performing a fall risk assessment, they are deemed to be at a higher risk of falling and consequently the sensitivity of the fall detection algorithm is increased (313), unless the fall detection algorithm is already operating at a higher sensitivity following 310 above. This increased sensitivity fall detection algorithm is then used in step 305 and subsequent steps to process the movement data to detect if a fall has occurred. If it is determined at 311 that the user device 4 is already in the data collection mode, the data collection mode is stopped and the timer deactivated (314). As the data collection mode has now ended, the user is assumed to no longer be performing the exercises or movements and consequently is not deemed to be at the higher risk of falling. Therefore the sensitivity of the fall detection algorithm can be reduced back to (or near to) the standard sensitivity (315). The method then continues from step 305.

If at 305 it is determined that the full fall detection algorithm is required then the processing unit 10 processes the measurements to determine if the user has fallen (317 and 319). If a fall is detected, the measurement data relating to the fall can be stored for later analysis, an alarm can be triggered and help requested from a call centre or emergency service (321).

In some embodiments, feedback can be provided to the fall detection system 2, for example from the service centre indicating whether the detected fall was an actual fall or a false alarm (322). This indication can be provided by personnel in the service centre following a conversation between the personnel and the user. Alternatively or in addition, feedback about whether the fall was an actual fall can be determined by the system 2 itself in response to a user pressing a button to revoke the alarm and/or by the system 2 detecting whether the user has stood up and/or is 'normally' active following a detected fall. After, 322, the data collection mode (or data analysis mode if active) is stopped (323) and any timer stopped. The sensitivity of the fall detection algorithm may then be adjusted (e.g. increased or decreased) based on whether the detected fall was an actual fall by the user. The device 4 then operates on the next block of measurement data (301).

If no fall is detected at 319 or the full fall detection processing is not triggered at 305, then the processing unit 10 checks for the second predefined gesture (307). If the second predefined gesture is recognized in the measurement data, then the user device 4 operates in the data analysis mode (325) in which all data stored during the or any data collection mode since the last time the data analysis mode was performed is processed to determine the fall risk. If the data analysis mode is activated in 325, the data collection mode (if still active) is switched off and any running timer stopped (323). In that case, the sensitivity of the fall detection algorithm will then be reduced back to a normal level (310) If the second predefined gesture is not recognised at 307, but at 308 the data collection mode is determined to be active, then it is checked at 327 whether the timer has expired (i.e. it is checked whether the time elapsed since the start of the data collection has reached a threshold value). If the timer has expired, then the data collection mode is deactivated (323). The sensitivity of the fall detection algorithm is then reduced or returned to the normal sensitivity level. If the timer has not yet expired, then the block of data received at 301 is stored (329).

After the data analysis mode is completed there will be a new or updated fall risk score for the user, and the sensitivity of the fall detection algorithm can be adjusted as appropriate based on the new or updated fall risk score.

The process then repeats for the next block of measurement data (301). The next block of measurement data may be contiguous with the previous block of measurement data (i.e. with no gaps between the blocks of data), non-contiguous with the previous block of measurement data or overlapping with the previous block of measurement data (e.g. the oldest sample or set of samples in the previous block of data can be discarded and a new sample or set of samples added to the remaining samples to form the next block of measurement data). Non-contiguous blocks of measurement data may be used where, for example, little or no movement is detected in the previous block of measurement data (e.g. because the user is lying or sitting down), which reduces the power consumption of the user device 4.

Although not shown in FIG. 9, if at any point a personal help button on the user device 4 is pressed by the user, the process moves straight to 321 and an alarm is triggered and help requested for the user by the user device 4.

There is therefore provided a system and method that enables falls to be more reliably detected when the user is engaging in a higher risk activity or their environment places them at a higher risk of falling, while largely keeping the occurrence of false alarms to a minimum.

While the invention has been illustrated and described in detail in the drawings and foregoing description, such illustration and description are to be considered illustrative or exemplary and not restrictive; the invention is not limited to the disclosed embodiments.

Variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A fall detection system for use in detecting falls by a user, the fall detection system comprising:
    a processing unit configured to determine context information about the user and/or an environment in which the user is located, and to increase a detection sensitivity of a fall detection algorithm used to detect falls by the user based on the determined context information indicating that the user is at an increased risk of falling, the increase in detection sensitivity occurring while the increased risk of falling is indicated by the determined context information.

2. The fall detection system of claim 1, wherein the context information comprises an indication of whether the user is performing a fall risk assessment test or balance training, and the processing unit is configured to determine that the user is at the increased risk of falling if the context information indicates that the user is performing the fall risk assessment test or the balance training.

3. The fall detection system of claim 1, wherein the context information comprises an indication of whether the user is walking, and the processing unit is configured to determine that the user is at the increased risk of falling if the context information indicates that the user is walking.

4. The fall detection system of claim 1, wherein the context information comprises an indication of whether an unusual movement pattern for the user has been detected, and the processing unit is configured to determine that the user is at the increased risk of falling if the context information indicates the unusual movement pattern.

5. The fall detection system of claim 1, wherein the context information comprises an indication of a current location of the user, and the processing unit is configured to determine that the user is at the increased risk of falling if the current location of the user is a known location where the user is at a higher risk of falling.

6. The fall detection system of claim 1, wherein the context information about the environment in which the user is located comprises an indication of an ambient light in the user's location, an indication of how even or uneven the ground is, an indication of a current weather or temperature and/or an indication of an ambient noise level and the processing unit is configured to determine that the user is at the increased risk of falling if the ambient light is below a threshold, if the ground is uneven, if the current weather is wet or the temperature is below a threshold and/or if the ambient noise level is above a threshold.

7. The fall detection system of claim 1, wherein the context information comprises an indication of a current time, and the processing unit is configured to determine that the user is at the increased risk of falling if the current time is within one or more specified time periods.

8. The fall detection system of claim 7, wherein the one or more specified time periods comprises night time and/or time periods shortly before and/or after a scheduled dose of medication.

9. The fall detection system of claim 1, wherein the context information comprises an indication of whether the user is making use of a required walking aid, whether the user is wearing their glasses, and/or an indication of a type of shoes the user is wearing, and the processing unit is configured to determine that the user is at the increased risk of falling if the user is not using the required walking aid, not wearing their glasses and/or not wearing their regular or the correct shoes.

10. The fall detection system of claim 1, wherein the context information comprises an indication of a current activity level of the user, and the context information indicates that the user is at the increased risk of falling if the current activity level is above a threshold activity level.

11. The fall detection system of claim 1, wherein the processing unit is further configured to determine if the context information indicates that the user is at a decreased risk of falling, and to decrease the detection sensitivity of the fall detection algorithm while the decreased risk of falling is indicated by the determined context information.

12. The fall detection system of claim 1, wherein the processing unit is configured to adjust the detection sensitivity of the fall detection algorithm by moving an operating point on a receiver operating characteristic curve, the receiver operating characteristic curve comprising a relation between detection probability and false alarm rate.

13. A method of operating a fall detection system to detect falls by a user, the method comprising:

in a processing unit:

determining context information about the user and/or an environment in which the user is located; and based on the determined context information indicating that the user is at an increased risk of falling, increasing a detection sensitivity of a fall detection algorithm used to detect falls by the user while the increased risk of falling is indicated by the determined context information.

14. The method of claim 13, the method further comprising:

determining further context information about the user and/or the environment in which the user is located; and resetting or reducing the detection sensitivity of the fall detection algorithm if the further context information indicates that the user is no longer at an increased risk of falling.

15. The method of claim 13, the method further comprising:

initially operating the fall detection system with the fall detection algorithm set to a normal detection sensitivity corresponding to a normal risk of falling for the user;

wherein when the context information indicates that the user is at an increased risk of falling relative to the normal risk of falling for the user, the detection sensitivity of the fall detection algorithm is increased above the normal detection sensitivity.

16. The method of claim 13, wherein the context information comprises an indication of whether the user is walking, the method further comprising determining that the user is at the increased risk of falling if the context information indicates that the user is walking.

17. The method of claim 13, wherein the context information comprises an indication of whether an unusual movement pattern for the user has been detected, the method further comprising determining that the user is at the increased risk of falling if the context information indicates the unusual movement pattern.

18. The method of claim 13, wherein the context information comprises an indication of a current location of the user, the method further comprising determining that the user is at the increased risk of falling if the current location of the user is a known location where the user is at a higher risk of falling.

19. The method of claim 13, wherein the context information about the environment in which the user is located comprises an indication of an ambient light in the user's location, an indication of how even or uneven the ground is, an indication of a current weather or temperature and/or an indication of an ambient noise level, the method further comprising determining that the user is at the increased risk of falling if the ambient light is below a threshold, if the ground is uneven, if the current weather is wet or the temperature is below a threshold and/or if the ambient noise level is above a threshold.

20. The method of claim 13, wherein the context information comprises an indication of a current time, wherein the method further comprising determining that the user is at the increased risk of falling if the current time is within one or more specified time periods, wherein the one or more specified time periods comprises night time and/or time periods shortly before and/or after a scheduled dose of medication.

21. A non-transitory computer program product having computer readable code embodied therein, the computer readable code being configured such that, on execution by a suitable computer or processing unit, the computer or processing unit performs a method of:

determining context information about a user and/or an environment in which the user is located; and based on the determined context information indicating that the user is at an increased risk of falling, increasing a detection sensitivity of a fall detection algorithm used to detect falls by the user while the increased risk of falling is indicated by the determined context information.

* * * * *